(12) United States Patent
Pendell-Jones

(10) Patent No.: US 7,545,490 B1
(45) Date of Patent: Jun. 9, 2009

(54) MICROSCOPE FLOW CELL APPARATUS FOR RAMAN ANALYSIS OF A LIQUID

(75) Inventor: James Everett Pendell-Jones, Baltimore, MD (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 394 days.

(21) Appl. No.: 11/526,670

(22) Filed: Sep. 26, 2006

(51) Int. Cl.
*G01N 21/01* (2006.01)
(52) U.S. Cl. ........................ 356/244; 356/246
(58) Field of Classification Search ................ 356/244, 356/246, 432–444; 250/373, 343, 576, 227.11, 250/227, 25
See application file for complete search history.

(56) References Cited

U.S. PATENT DOCUMENTS

| | | | | |
|---|---|---|---|---|
| 4,175,233 A | * | 11/1979 | DePalma et al. | 250/343 |
| 4,180,739 A | * | 12/1979 | Abu-Shumays | 250/461.1 |
| 4,181,853 A | * | 1/1980 | Abu-Shumays et al. | 250/304 |
| 4,822,166 A | * | 4/1989 | Rossiter | 356/246 |
| 4,823,168 A | * | 4/1989 | Kamahori et al. | 356/246 |
| 5,140,169 A | * | 8/1992 | Evens et al. | 250/576 |
| 5,410,403 A | * | 4/1995 | Wells | 356/335 |
| 5,917,606 A | * | 6/1999 | Kaltenbach | 356/440 |
| 6,188,474 B1 | * | 2/2001 | Dussault et al. | 356/246 |
| 6,307,204 B1 | * | 10/2001 | Kanomata et al. | 250/373 |
| 6,388,746 B1 | | 5/2002 | Eriksson et al. | |
| 6,526,188 B2 | | 2/2003 | Dourdeville et al. | |
| 7,068,365 B2 | | 6/2006 | Hansen et al. | |

\* cited by examiner

*Primary Examiner*—Sang Nguyen
(74) *Attorney, Agent, or Firm*—Edell, Shapiro & Finnan, LLC

(57) ABSTRACT

A flow cell apparatus is provided comprising a body having a first surface, an inlet port and an outlet port. A channel is provided in the body having a first end and a second end. In one embodiment, the channel is sized so as to have a depth that allows for sufficient excitation and illumination of solutions or particles contained in a liquid to be analyzed. The inlet port is coupled to the first end of said channel and the outlet port is coupled to the second end of said channel. A window of optically transparent material overlies at least a portion of the channel to provide optical access to the liquid in the channel.

13 Claims, 5 Drawing Sheets

MICROSCOPE FLOW CELL APPARATUS FOR RAMAN ANALYSIS OF A LIQUID

BACKGROUND OF THE INVENTION

There are situations where it is desirable to monitor a flow of a liquid for certain substances. For example, it may desirable to detect harmful chemical or biological substances in a water supply.

While various fluid or liquid capturing devices are known, there is a need for a flow cell apparatus that is inexpensive and can be easily disassembled for cleaning or replacing parts, while still providing for a reliable sample volume of liquid for monitoring.

SUMMARY OF THE INVENTION

Briefly, a flow cell apparatus comprising a body having a first surface, an inlet port and an outlet port. A channel is provided in the body. In one embodiment, the channel is sized so as to have a depth that allows for sufficient excitation and illumination of solutions or particles contained in a liquid to be analyzed. The inlet port is coupled to a first end of the channel and the outlet port is coupled to a second end of the channel. A window of optically transparent material overlies at least a portion of the channel to provide optical access to the liquid in the channel.

DETAILED DESCRIPTION

Figure 1:
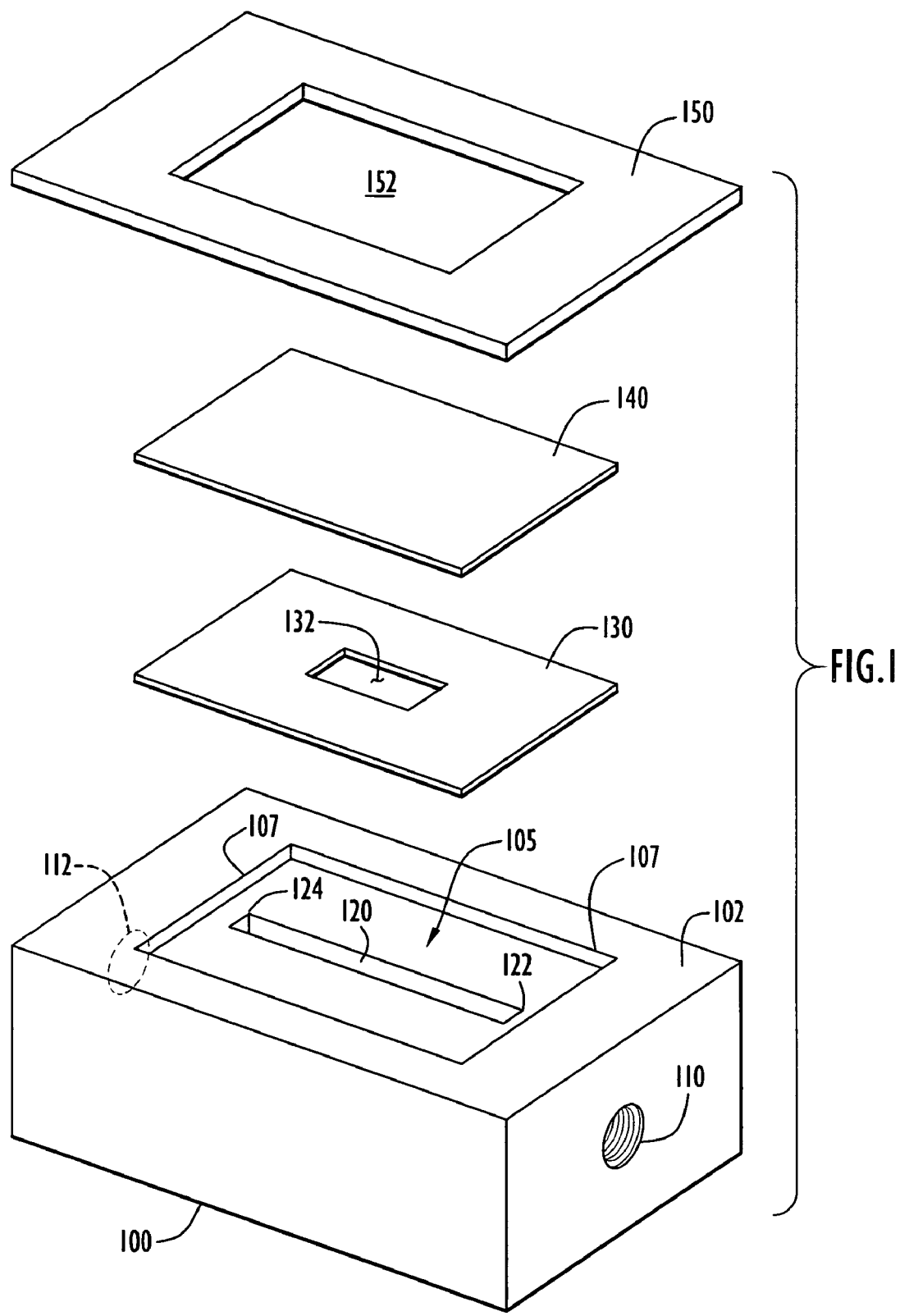
FIG. 1 is an exploded perspective view of the flow cell apparatus according to an embodiment of the invention.

Referring first to FIG. 1, the flow cell apparatus 10 according to an embodiment of the present invention is described. The flow cell apparatus comprises a body 100 having a first (top) surface 102. There is a recess or cavity 105 in the first surface 102 having a ledge 107 around the perimeter thereof. Said another way, the cavity 105 is recessed into the first surface 102 of the body 100. The cavity 105 is open along the first surface 102. The body 100 also has an inlet port or opening 110 and an outlet port 112 or opening. There is a channel 120 formed in the recess 105 and the channel 120 comprises a first end 122 and a second end 124. The inlet port 110 is coupled to or in communication with the first end 122 of the channel 120 and the outlet port 112 is coupled to or in communication with the second end 124 of the channel 120.

In one embodiment, the body 100 may be made of stainless steel material which is relatively inert. In addition, stainless steel is conducive to thermo-electric cooling and heating. However, it should be understood that the body may be made of any other suitable material.

A gasket 130 fits into the recess or cavity 105 on the first surface 102 of the body 100. The gasket 130 overlies the channel 120 and the perimeter edges of the gasket 130 rest on the ledge 107 that extends around the perimeter of the recess 105. The gasket 130 comprises a slot or aperture 132 in a central position thereof. The aperture 132 defines an optical interrogation field of view of the channel 120. There are numerous types of materials that may be used for the gasket 130. For example, the gasket 130 may be made of silicone material. However, it may be interchangeable for gaskets of other materials depending on the nature of the liquid/fluid that is to be analyzed.

Figure 2:
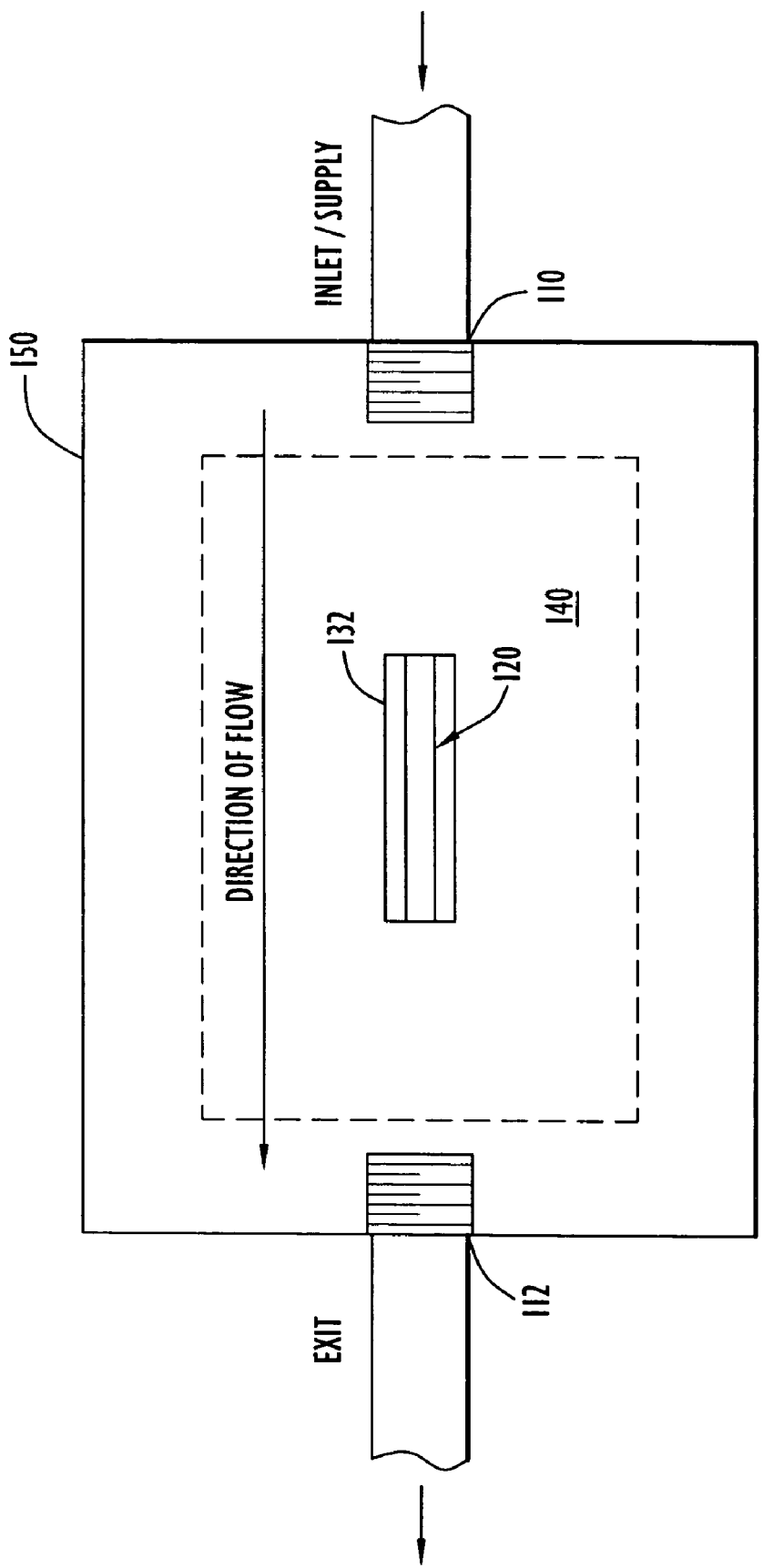
FIG. 2 is a top view of the flow cell apparatus according to an embodiment of the invention.
Figure 3:
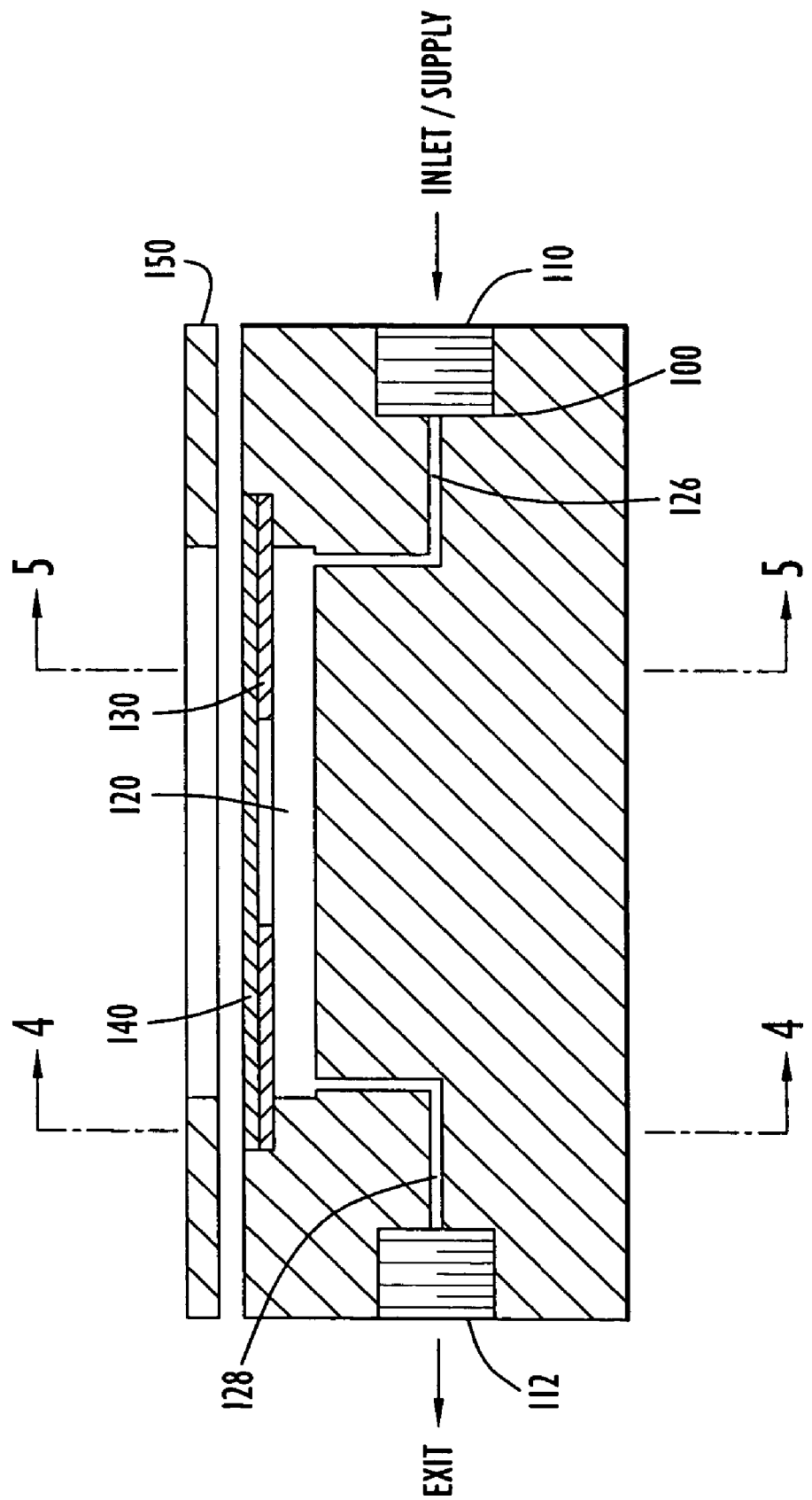
FIG. 3 is a side view of the flow cell apparatus according to an embodiment of the invention.

Reference is now made to FIGS. 2 and 3, with continued reference to FIG. 1. A window 140 fits over the gasket 130 in the recess 105 such that a top surface of the window 140 is substantially flush with the first surface 102 of the body 100. The window 140 may be made of used silica glass material or other material suitable to pass light in the ultraviolet wavelength region.

As shown in FIG. 2, the aperture or slot 132 in the gasket provides optical access to at least a portion of the channel 120 inside the body 100 as fluid or liquid flows in the channel 120 from the inlet port 110 to the outlet port 112. The inlet port 110 and outlet port 112 may have a threaded wall surface to enable threaded connection to a supply conduit at the inlet port 110 and to a waste or exit conduit at the outlet port 112. A pump (not shown) may drive a flow of a fluid or liquid to be monitored to the inlet port 110.

FIG. 3 further shows that there is a coupling passageway 126 between the inlet port 110 and the first end 122 of the channel. Similarly, there is a coupling passageway 128 between the second end 124 of the channel and the outlet port 112.

Figure 5:
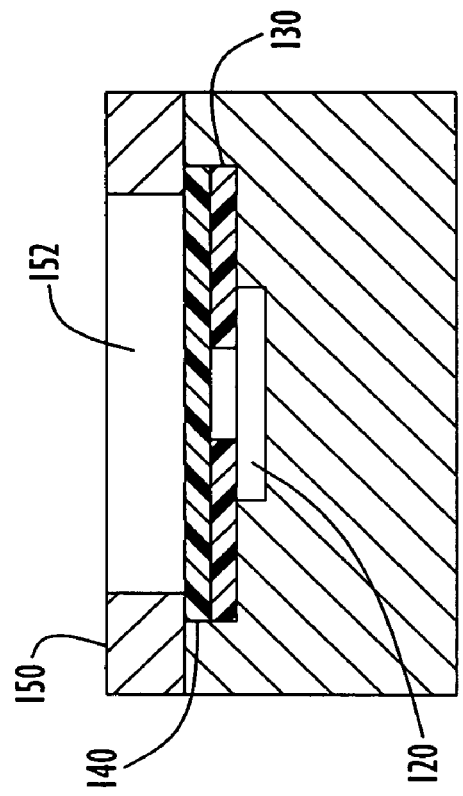
FIG. 5 is a cross-sectional view taken through line 5-5 of FIG. 3.
Figure 4:
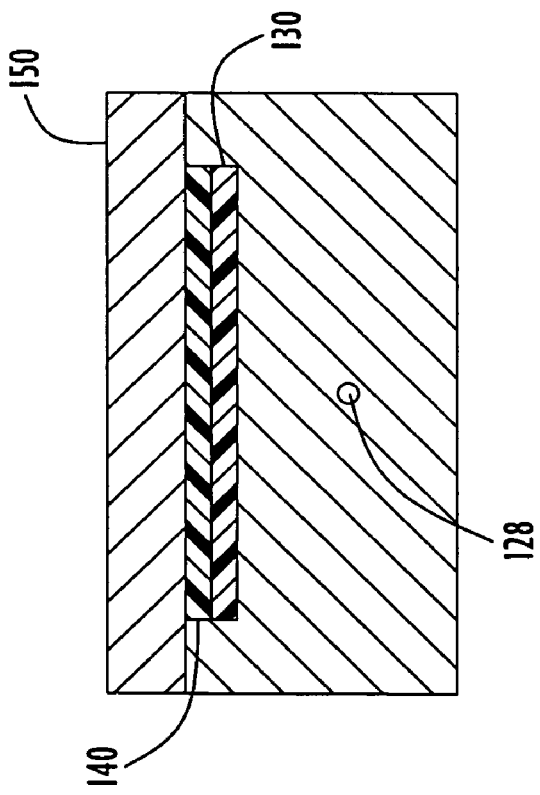
FIG. 4 is a cross-sectional view taken through line 4-4 of FIG. 3.

Reference is now made to FIGS. 4 and 5, with continued reference to FIGS. 1-3. There is a retaining plate or lid 150 that fits onto the body 100 over the window 140 to secure the window 140 and gasket in place in the recess 105. The retaining plate 150 has an aperture 152 to permit optical access to the window 140. The retaining plate 150 may removably attach to the body 100 by screws, snap fit, etc. In one embodiment, the retaining plate 150 is secured to the body 100 by hex screws. Furthermore the body 100 and retaining plate 150 also may have complementary guide posts and guide holes to aid in alignment and quick assembly of the flow cell device.

The dimensions of the flow cell apparatus 10 may vary depending on the application and the liquid to be monitored. In one embodiment, and by way of example only, the flow cell apparatus 10 is designed to monitor whole water samples. The flow cell apparatus 10 is designed to minimize the introduction of air bubbles into the sensing volume. The collection volume is designed to maximize interaction of an illumination laser with the particulate samples contained in the collection volume. For example, the apparatus 10 may be designed to match the collection volumes of a 15× Cassagrain type microscope objective. Also, the apparatus 10 is designed to be easy to disassemble in order to clean or replace its parts.

In one embodiment, the channel 120 is designed to have depth of 1 to 2 mm to allow for sufficient excitation and illumination of solutions or particulate samples. However, the channel 120 may be designed to have a different depth for samples that may be highly absorptive. For example, to ensure that certain substances, such as spores, pass through the focal volume, the channel may have a depth of 1 mm or smaller. For samples such as dilute chemicals that are not absorptive, a channel depth of 2 mm may be suitable to ensure that the focal volume (or path length) is maximized. Thus, one exemplary set of dimensions for the cell body is a cross-sectional area of 1.5×1.5 inches, the window is 1×1 inches and the length of the aperture or slot is 0.5 inches.

To clean or replace the parts of the flow cell apparatus 10, the retaining plate 150 is removed allow for access to the window 140 and the gasket 130. The channel 120 can be cleaned once the window 140 and gasket 130 are removed. In addition, the gasket 130 and window 140 may be cleaned or replaced with a new gasket and/or window. In particular, the window 140 may be made of relatively inexpensive material as long as it is transparent to the incoming and exiting light.

An alternative to the configuration shown in FIGS. 1-5, the window 140 may fit directly onto the body 100 in the recess 105 and the gasket 130 positioned on top or over the window 140. In this configuration, the window 140 seals the channel 120.

Figure 6:
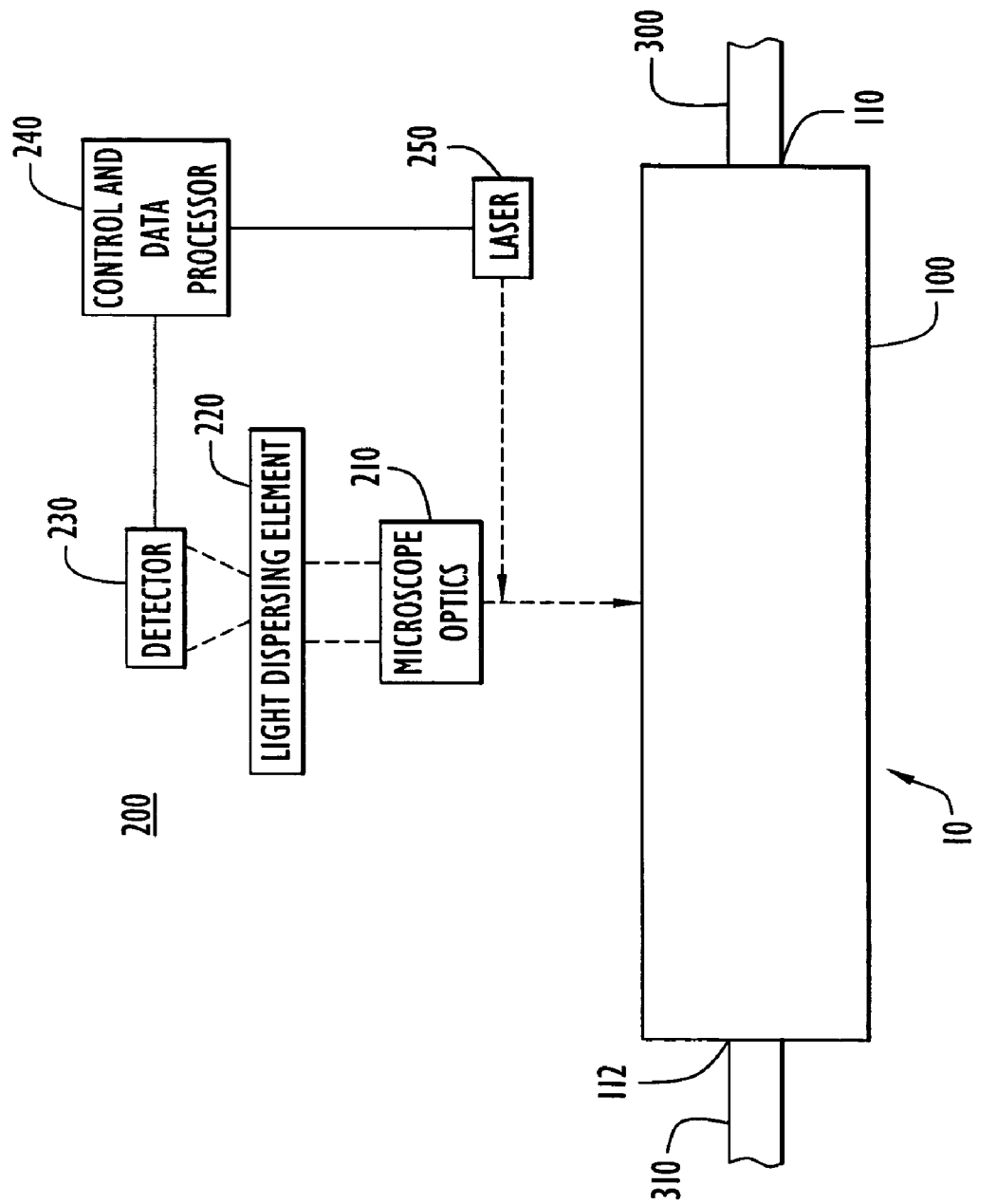
FIG. 6 is a schematic diagram showing the flow cell apparatus as part of a spectroscopy analysis system according to an embodiment of the invention.

Turning to FIG. 6, operation of the flow cell apparatus 10 as part of an optical interrogation and analysis system 200 will be described. The flow cell apparatus 10 is attached at the inlet port 110 to a conduit or line 300 of a liquid to be analyzed and the outlet port 112 is connected to an exhaust or exit line 310. The optical interrogation and analysis system 200 comprises microscope optics 210, a light dispersing element 220 such as a grating or prism, a detector 230 such as an intensified charged coupled device (ICCD), a control and data processor 240 and a laser 250. The flow cell apparatus 10 is positioned beneath the microscope optics 210 at a suitable distance within the focal range of the microscope optics 210.

With reference to FIGS. 1-3 in conjunction with FIG. 6, in operation, the control and data processor 240 activates the laser 250 to emit a beam of light, such as light in the ultraviolet wavelength region (or other wavelength regions) that is directed to the aperture 132 (FIGS. 1-3) and through the window 140 to a sample volume of fluid passing through the channel 120. As mentioned above, one application of the flow cell apparatus is to interface to a microscope and enable Raman analysis of whole water samples. In the case of a Raman or fluorescence scattering technique, the fluid will return optical energy based on its interaction or excitation with the beam of light. The returned optical energy is collected by the microscope optics 210. The microscope optics 210 focuses the returned optical energy to a light dispersing element 220 that disperses the returned optical energy into its constituent wavelengths and onto a detector 230. The detector 230 produces spectrum data, such as Raman spectrum data or fluorescence spectrum data, depending on the type of scattering in the returned optical energy. The control and data processor 240 then analyzes the spectrum data produced by the detector 230 to detect and identify substances of a chemical or biological origin in the fluid passing through the flow cell apparatus 10.

The system and methods described herein may be embodied in other specific forms without departing from the spirit or essential characteristics thereof. The foregoing embodiments are therefore to be considered in all respects illustrative and not meant to be limiting.

What is claimed is:

1. A flow cell apparatus, comprising:
a body having a first surface, an inlet port and an outlet port;
a channel in said body having a first end and a second end, wherein the channel is sized so as to have a depth that allows for sufficient excitation and illumination of solutions or particles contained in a liquid to be analyzed, wherein the channel is open facing towards the first surface of the body, and the inlet port being coupled to the first end of said channel and the outlet port being coupled to the second end of said channel, the body comprising a recess in said first surface around at least a perimeter of the channel;
a gasket that is sized and configured to removably fit into the recess and to overly the channel, wherein the gasket comprises an aperture that defines an optical interrogation field of view to the channel for optical energy that is directed from exterior of the body towards the first surface of the body and for optical energy emitted or scattered from the channel through the aperture and out of the body via the first surface of the body;
a window of optically transparent material that is configured to removably fit into the recess overlying the gasket and configured to pass optical energy through the aperture of the gasket to and from the channel.

2. The apparatus of claim 1, and further comprising a ledge around at least a portion of the perimeter of the channel, wherein the gasket is configured to removably fit into the recess and has peripheral edges that rest on the ledge beneath the window.

3. The apparatus of claim 1, and further comprising a retaining member that removably fits onto the body at said first surface so as to secure the window and gasket in position over the channel.

4. The apparatus of claim 1, wherein the channel is sized to have a depth of up to 2 mm.

5. The apparatus of claim 1, wherein the body is formed of an inert material.

6. The apparatus of claim 1, wherein the body is formed of thermally conductive material.

7. The apparatus of claim 1, wherein the window is formed of material that passes ultraviolet light.

8. The apparatus of claim 1, wherein the gasket is configured and arranged in the body so as to provide the only path for optical energy into the apparatus from the first surface of the body and out of the apparatus through the first surface of the body.

9. A flow cell apparatus, comprising:
a body having a first surface, an inlet port and an outlet port;
a cavity in the body that is recessed into the first surface, the cavity being open along the first surface;
a channel in said cavity having a first end and a second end, the inlet port being coupled to the first end of said channel and the outlet port being coupled to the second end of said channel, wherein the channel is open facing towards the first surface of the body;
a gasket that is sized and configured to removably fit in said cavity and around at least a portion of the perimeter of the channel so as to overly the channel, wherein the gasket comprises an aperture that defines an optical interrogation field of view into the channel for optical energy that is directed from exterior of the body towards the first surface of the body and for optical energy emitted or scattered from the channel through the aperture and out of the body via the first surface of the body;
a window of optically transparent material that is configured to removably fit in said cavity overlying the gasket and configured to pass optical energy through the aperture of the gasket to and from the channel; and
a retaining plate that removably attaches to the body at said first surface over the window so as to secure the window and gasket in the cavity.

10. The apparatus of claim 9, and further comprising a ledge around at least a portion of the perimeter of the channel, wherein peripheral edges of the gasket rest on the ledge.

11. The apparatus of claim 9, wherein the channel is sized so as to have a depth that allows for sufficient excitation and illumination of solutions or particles contained in a liquid to be analyzed.

12. The apparatus of claim 9, wherein the channel is sized to have a depth of up to 2 mm.

13. The apparatus of claim 9, wherein the gasket is configured and arranged in the body so as to provide the only path for optical energy into the apparatus from the first surface of the body and out of the apparatus through the first surface of the body.

* * * * *